(12) United States Patent
Friedrich et al.

(10) Patent No.: US 7,229,803 B2
(45) Date of Patent: Jun. 12, 2007

(54) REACTION OF (DI)AMINES IN THE PRESENCE OF A LYSINE OXIDASE AND OF A REDUCING AGENT

(75) Inventors: Thomas Friedrich, Darmstadt (DE); Norbert Zimmermann, Deidesheim (DE); Rainer Stürmer, Rödersheim-Gronau (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 417 days.

(21) Appl. No.: 10/474,601

(22) PCT Filed: Apr. 8, 2002

(86) PCT No.: PCT/EP02/03873

§ 371 (c)(1),
(2), (4) Date: Apr. 7, 2004

(87) PCT Pub. No.: WO02/086138

PCT Pub. Date: Oct. 31, 2002

(65) Prior Publication Data

US 2004/0158061 A1    Aug. 12, 2004

(30) Foreign Application Priority Data

Apr. 9, 2001  (DE) ............................... 101 17 730

(51) Int. Cl.
| C12P 17/00 | (2006.01) |
| C12P 17/10 | (2006.01) |
| C12P 13/00 | (2006.01) |
| C12P 11/00 | (2006.01) |
| C12P 7/02  | (2006.01) |

(52) U.S. Cl. ............ 435/117; 435/121; 435/128; 435/130; 435/135; 435/136; 435/146; 435/155; 435/156; 435/158; 540/609; 544/59; 544/170; 544/399; 546/248; 548/571; 548/950

(58) Field of Classification Search ........... 435/117, 435/121, 128, 130, 135–136, 146, 155–156, 435/158, 145; 540/609; 544/59, 170, 399; 546/248; 548/571, 950
See application file for complete search history.

(56) References Cited

U.S. PATENT DOCUMENTS

| 6,039,982 A  * | 3/2000 | Wagner et al. ............... 426/18 |
| 6,211,434 B1 * | 4/2001 | Duvick et al. ............. 800/279 |
| 6,440,937 B1   | 8/2002 | Baucke et al. |
| 6,455,671 B1   | 9/2002 | Böhm et al. |
| 2003/0004308 A1| 1/2003 | Böhm et al. |

FOREIGN PATENT DOCUMENTS

| DE | 19840069 A1   | 3/2000 |
| WO | WO 94/29336 A1 | 12/1994 |
| WO | WO 95/35309 A1 | 12/1995 |
| WO | WO 98/04523 A1 | 2/1998 |
| WO | WO 98/06740 A1 | 2/1998 |

OTHER PUBLICATIONS

Askin et al. "Highly diastereoselective reaction of a chiral, non-racemic amide enolate with (S)-Glycidyl Tosylate. Synthesis of the orally active HIV-1 protease inhibitor L- 735,524." *Tetrahedron Letters*, 1994;35(5):673-76.
Kuchar et al. "Cloning, sequence analysis, and characterization of the 'Lysyl oxidase' from *Pichia pastoris*." *J. Inorg. Biochem.* 2001;83(2-3):193-204.
Kusakabe et al. "A new antitumor enzyme, L-lysine alpha-oxidase from *Trichoderma viride*. Purification and enzymological properties." *J. Biol. Chem.* Feb. 10, 1980;255(3):976-81.
Shah et al. "Reaction of lysyl oxidase with trans-2-phenylcyclopropylamine." *J. Biol. Chem*, Jun. 5, 1993;268(16):11580-5.
Tur et al. "Unprecedented lysyloxidase activity of *Pichia pastoris* benzylamine oxidase." *FEBS Lett.* Sep. 26, 1988;238(1):74-6.
Weber et al. "L-Lysine α-oxidase from *Trichoderma viride* i4. Purification and characterization" *J. Basic Microbiol.* 1994;34(4):265-76.

* cited by examiner

*Primary Examiner*—Herbert J. Lilling
(74) *Attorney, Agent, or Firm*—Lahive & Cockfield, LLP; Elizabeth A. Hanley; Maria Laccotripe Zacharakis

(57) ABSTRACT

The invention relates to methods for reacting (di)amines as substrates in the presence of a lysine oxidase arid a reducing agent, resulting in alcohols, diols or cyclic secondary amines. In a particular embodiment, the invention is directed to methods of preparing cyclic secondary amines suitable for ultimately synthesizing piperidine-2-carboxylic acid and proline derivatives, useful, for example as thrombin inhibitors.

11 Claims, No Drawings

SEQUENCE LISTING

<160> NUMBER OF SEQ ID NOS: 12

<210> SEQ ID NO 1
<211> LENGTH: 25
<212> TYPE: PRT
<213> ORGANISM: Pichia pastoris
<220> FEATURE:
<221> NAME/KEY: VARIANT
<222> LOCATION: 2
<223> OTHER INFORMATION: Xaa = Any Amino Acid, probably Ser
<220> FEATURE:
<221> NAME/KEY: VARIANT
<222> LOCATION: 3
<223> OTHER INFORMATION: Xaa = Any Amino Acid, probably Cys
<220> FEATURE:
<221> NAME/KEY: VARIANT
<222> LOCATION: 5
<223> OTHER INFORMATION: Xaa = Any Amino Acid, probably Cys
<220> FEATURE:
<221> NAME/KEY: VARIANT
<222> LOCATION: 21
<223> OTHER INFORMATION: Xaa = Any Amino Acid, probably Cys
<220> FEATURE:
<221> NAME/KEY: VARIANT
<222> LOCATION: 24
<223> OTHER INFORMATION: Xaa = Any Amino Acid, probably Leu
<220> FEATURE:
<221> NAME/KEY: VARIANT
<222> LOCATION: 25
<223> OTHER INFORMATION: Xaa = Any Amino Acid, probably Ser

<400> SEQUENCE: 1

Gly Xaa Xaa Gln Xaa Lys Thr Asn Glu Lys Val Asn Ile Glu Ala Pro
 1               5                  10                  15

Lys Pro Asn Ile Xaa Asp Thr Xaa Xaa
            20                  25

<210> SEQ ID NO 2
<211> LENGTH: 13
<212> TYPE: PRT
<213> ORGANISM: Pichia pastoris
<220> FEATURE:
<221> NAME/KEY: VARIANT
<222> LOCATION: 4
<223> OTHER INFORMATION: Xaa = Any Amino Acid, probably Cys

<400> SEQUENCE: 2

Glu Tyr Pro Xaa Ala Pro Gly Val Val Tyr Asn Thr Lys
 1               5                  10

<210> SEQ ID NO 3
<211> LENGTH: 15
<212> TYPE: PRT
<213> ORGANISM: Pichia pastoris

<400> SEQUENCE: 3

Gly Gly Thr Tyr Ser Thr Val Thr Gln Asn Pro Thr Leu Asn Arg
 1               5                  10                  15

<210> SEQ ID NO 4
<211> LENGTH: 13
<212> TYPE: PRT
<213> ORGANISM: Pichia pastoris
<220> FEATURE:
<221> NAME/KEY: VARIANT
<222> LOCATION: 10
<223> OTHER INFORMATION: Xaa = Any Amino Acid

<400> SEQUENCE: 4

```
Asp Tyr Asn Ile Met Pro Gly Gly Gly Xaa Val His Arg
 1               5                  10
```

```
<210> SEQ ID NO 5
<211> LENGTH: 13
<212> TYPE: PRT
<213> ORGANISM: Pichia pastoris
<220> FEATURE:
<221> NAME/KEY: VARIANT
<222> LOCATION: 10
<223> OTHER INFORMATION: Xaa = Any Amino Acid

<400> SEQUENCE: 5

Ala Thr Gly Gly Thr Tyr Ser Thr Val Xaa Ala Gln Asn
 1               5                  10
```

```
<210> SEQ ID NO 6
<211> LENGTH: 9
<212> TYPE: PRT
<213> ORGANISM: Pichia pastoris

<400> SEQUENCE: 6

Ala Pro Glu Thr Glu Asn Asn Ala Arg
 1               5
```

```
<210> SEQ ID NO 7
<211> LENGTH: 19
<212> TYPE: PRT
<213> ORGANISM: Pichia pastoris
<220> FEATURE:
<221> NAME/KEY: VARIANT
<222> LOCATION: 4
<223> OTHER INFORMATION: Xaa = Any Amino Acid, probably Pro
<220> FEATURE:
<221> NAME/KEY: VARIANT
<222> LOCATION: 8
<223> OTHER INFORMATION: Xaa = Any Amino Acid, probably Glu

<400> SEQUENCE: 7

Gly Pro Leu Xaa Val Asn Glu Xaa Thr Thr Ile Glu Pro Leu Ser Phe
 1               5                  10                  15

Tyr Asn Thr
```

```
<210> SEQ ID NO 8
<211> LENGTH: 28
<212> TYPE: PRT
<213> ORGANISM: Pichia pastoris

<400> SEQUENCE: 8

Ile Tyr Glu Leu Ser Leu Gln Glu Leu Ile Ala Glu Tyr Gly Ser Asp
 1               5                  10                  15

Asp Pro Asn Asn Gln His Thr Phe Tyr Ser Asp Ile
            20                  25
```

```
<210> SEQ ID NO 9
<211> LENGTH: 13
<212> TYPE: PRT
<213> ORGANISM: Pichia pastoris

<400> SEQUENCE: 9

Asp Asn Val Asp Asp Leu Ser Cys Thr Ile Ile Gln Arg
 1               5                  10
```

```
<210> SEQ ID NO 10
<211> LENGTH: 10
```

```
<212> TYPE: PRT
<213> ORGANISM: Pichia pastoris

<400> SEQUENCE: 10

Val Ala Pro Glu Thr Glu Asn Cys Ala Arg
1               5                   10

<210> SEQ ID NO 11
<211> LENGTH: 17
<212> TYPE: PRT
<213> ORGANISM: Pichia pastoris

<400> SEQUENCE: 11

Asn Val Asp Val Glu Tyr Pro Cys Ala Pro Gly Val Val Tyr Asn Thr
1               5                   10                  15
Lys

<210> SEQ ID NO 12
<211> LENGTH: 12
<212> TYPE: PRT
<213> ORGANISM: Pichia pastoris
<220> FEATURE:
<221> NAME/KEY: VARIANT
<222> LOCATION: 8
<223> OTHER INFORMATION: Xaa = Any Amino Acid, probably Ser
<220> FEATURE:
<221> NAME/KEY: VARIANT
<222> LOCATION: 11
<223> OTHER INFORMATION: Xaa = Phe or Glu

<400> SEQUENCE: 12

Gly Tyr Pro Asn Ala Glu Tyr Xaa Leu Asp Xaa Arg
1               5                   10
```

REACTION OF (DI)AMINES IN THE PRESENCE OF A LYSINE OXIDASE AND OF A REDUCING AGENT

RELATED APPLICATIONS

This application claims the benefit of German Application Ser. No. 10117730.5, filed Apr. 9, 2001, the entire contents of which are incorporated herein by this reference.

The invention relates to methods for reacting (di)amines as substrates in the presence of a lysine oxidase and of a reducing agent. Depending on the substrate, this results in alcohols, diols or cyclic secondary amines.

The invention further relates to the use of a lysine oxidase in said methods.

Proline derivatives are important intermediates for thrombin inhibitors (WO 95/35309, WO 98/06740, WO 94/29336), and piperazine-2-carboxylic acid derivatives are used in HIV protease inhibitors. Preparation of such cyclic secondary araines such as piperazine-2-carboxylic acid, piperidine-2-carboxylic acid and proline derivatives frequently requires great synthetic complexity, as described by D. Askin et al. in Tetrahedron Lett. 1994, 35(5), 673–676 and in WO 98/04523. A method for preparing partly unsaturated piperidine-2-carboxylic acid derivatives which is rather simple by comparison starts from L-lysine. Its α-amino group is oxidized in the presence of oxygen to the keto group with formation of $H_2O_2$ and $NH_3$, to result in 2-oxo-6-aminohexanoic, as described in J. Basic Microbiol. 1994, 34(4), 265–276. If this reaction takes place in the presence of catalase, the resulting 2-oxo-6-aminohexanoic acid is cyclized to 1,2-didehydropiperidine-2-carboxylic acid. In order to prepare piperidine-2-carboxylic acid therefrom it would be necessary to reduce the 1,2-didehydropiperidine-2-carboxylic acid in an additional process step after purification.

It is an object of the present invention to find a further method for preparing cyclic secondary amines which is suitable for synthesizing piperidine-2-carboxylic acid and proline derivatives.

We have found that this object is achieved by a method for reacting amines of the general formula (I)

$$A-CH_2-NH_2 \quad (I)$$

with A- meaning

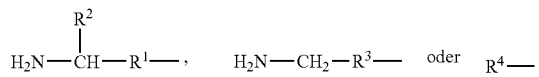

to give compounds of the general formula (II) or (III)

with B- meaning $HO-CH_2-R^3-$ or $R^4-$ comprising the following steps:
a) oxidation of at least one

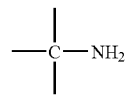

group of an amine of the general formula (I) to a carbonyl group in the presence of a lysine oxidase as catalyst;

b) where appropriate reaction of the second $NH_2$ group of an amine of the general formula (I) with

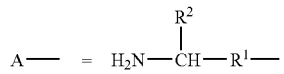

With the carbonyl group resulting from a) to give an enamine or imine by cyclization;

c) reduction of the carbonyl group(s) resulting from a), or of the enamine or imine resulting where appropriate from b), with a reducing agent respectively to hydroxymethyl groups or to a cyclic secondary amine of the general formula (II), where $R^1$ is $NR^5$ or a linear bivalent $C_2$–$C_6$ hydrocarbon radical which is optionally substituted by $CO_2H$, $CO_2R^6$, OH, SH and/or $N(R^5)_2$ and/or contains nonadjacent O, S and/or N atoms, where $R^5$ is H or linear $C_1$–$C_6$-alkyl and $R^6$ is linear $C_1$–$C_6$-alkyl or branched $C_3$–$C_6$, $C_6$–$C_{10}$-aryl, and $R^2$ is H, $CO_2H$, $CO_2R^6$ or CN, where the method is carried out as a one-pot method, lysine oxidase and reducing agent are present together, and in the definition of A in the general formula (I)

$R^3$ is a bivalent $C_0$–$C_1$ or $C_5$–$C_{18}$ hydrocarbon radical which is optionally substituted by linear $C_1$–$C_6$-alkyl or branched $C_3$–$C_6$-alkyl, $C_6$–$C_{10}$-aryl, $C_4$–$C_{10}$-heteroaryl and/or $CO_2R^6$ and/or contains nonadjacent O, S and/or N atoms, and $R^4$ is a linear $C_1$–$C_{20}$ hydrocarbon radical which is optionally substituted by functional groups such as $CO_2H$ and/or $CO^2R^6$ and/or contains nonadjacent O, S and/or N atoms.

It is all the more surprising to carry out the method of the invention as one-pot method since it was not to be expected that lysine oxidases retain their activity in the presence of a reducing agent. Purification of the cyclic enamines or imines resulting from b) or the compounds with at least one carbonyl group resulting from a) before reduction to cyclic secondary amines of the general formula (II) or alcohols of the general formula (III) is therefore unnecessary. In addition, step b) of the method of the invention, the cyclization to the enamine or imine, takes place spontaneously even without addition of catalase, in contrast to the known method.

Depending on the structure of the amine of the general formula (I), the substrate, the individual steps of the method of the invention proceed in detail as follows:

1) If an amine of the general formula (I) with

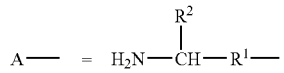

where $R^1$ and $R^2$ have the abovementioned meaning is employed, the substrate is a diamine. In step a) of the method of the invention, one of the two

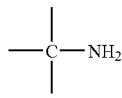

groups of this diamine is oxidized to a carbonyl group with catalysis by a lysine oxidase. It has been observed that one use of the lysine oxidase from *Pichia pastoris* there is oxidation exclusively of the ε-amino group and not of the α-amino group of L- and D-lysine. However, it is immaterial for the following steps which amino group has been oxidized or whether an aldehyde or a ketone is present. The carbonyl group generated in step a) then reacts spontaneously in step b) with the second—unreacted—amino group to give a Schiff's base (an imine) or an enamine. Since this is an intramolecular reaction it results in a cyclic enamine or imine. The latter can also be isolated. The method of the invention is, however, such that an isolation is unnecessary before step c) because steps a) to c) are carried out as a one-pot method. In step c), the cyclic enamine or imine is then reduced by a reducing agent present in the substrate solution to a cyclic secondary amine of the general formula (II).

2) If an amine of the general formula (I) with A-=$H_2N$—$CH_2$—$R^3$— where $R^3$ has the abovementioned meaning is employed, the substrate is a diamine with two aminomethyl groups. Both aminomethyl groups are oxidized in step a) of the method of the invention in the presence of a lysine oxidize as catalyst to formyl groups. In contrast to 1), an intramolecular reaction is not possible to not favored and therefore does not take place. Both formyl groups are then reduced in step c) with a reducing agent to hydroxymethyl groups to form an alcohol of the general formula (III) with B-=HO—$CH_2$—$R^3$—.

3) If an amine of the general formula (I) with A=$R^4$ where $R^4$ has the meaning indicated above is employed, its aminomethyl group is oxidized to a formyl group. This formyl group is then reduced in step c) of the method of the invention by the reducing agent present in the substrate solution to a hydroxymethyl group to form a primary alcohol of the general formula (III) with B=$R^4$.

The methods of the invention can be described in detail as follows:

1) Method for preparing cyclic secondary amines of the general formula (II) from diamines of the general formula (Ia)

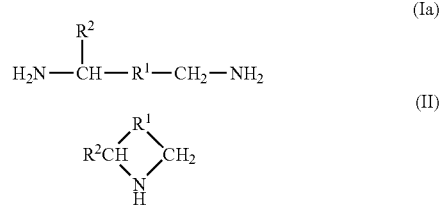

where $R^1$ is $NR^5$ or a linear bivalent hydrocarbon radical with 2 to 6 C atoms, which is optionally substituted by functional groups such as $CO_2H$, $CO_2R^6$, OH, SH and/or $N(R^5)_2$, and/or contains nonadjacent heteroatoms such as O, S, N, where $R^5$ is H or linear $C_1$–$C_6$-alkyl and $R^6$ s linear $C_1$–$C_6$-alkyl or branched $C_3$–$C_6$-alkyl $C_6$–$C_{10}$-aryl, and $R^2$ is H, $CO_2H$, $CO_2R^6$ or CN, comprising the following steps:
a) oxidation of one of the two

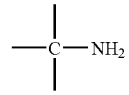

groups of a diamine of the general formula (Ia) to a carbonyl group in the presence of a lysine oxidase as catalyst;
b) reaction of the second $NH_2$ group of the diamine of the general formula (Ia) with the carbonyl group resulting from step a) to give an enamine or imine by cyclization;
c) reduction of the enamine or imine resulting from b) with a reducing agent to give a cyclic secondary amine of the general formula (II);

wherein the method is carried out as one-pot method, and lysine oxidase and reducing agent are present together.

In the definition of the radical $R^1$, the term "hydrocarbon radical" also encompasses (partially) unsaturated hydrocarbon radicals with cis double bonds.

Examples of suitable diamines of the general formula (Ia) are basic amino acids such as D- and L-lysine and D- and L-ornithine, 2,6-diamino4-azahexanoic acid, and 1,6-diaminohexane. L-lysine and L-ornithine are preferably employed. Use of L-lysine results in piperidine-2-carboxylic acid, and use of L-ornithine results in proline.

2) Method for preparing diols of the general formula (IIIa) from diamines of the general formula (Ib)

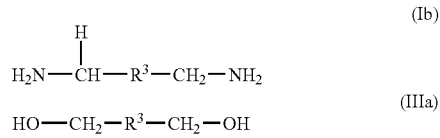

comprising the following steps:
a) oxidation of the two aminomethyl groups of a diamine of the general formula Ib) to formyl groups in the presence of a lysine oxidase as catalyst;
b) reduction of the formyl groups resulting from a) with a reducing agent to hydroxymethyl groups to form a diol of the general formula (IIIa);

wherein the method is carried out as one-pot method, lysine oxidize and reducing agent are present together, and $R^3$ is a bivalent $C_0$–$C_1$ or $C_5$–$C_{18}$ hydrocarbon radical which is optionally substituted by linear $C_1$–$C_6$-alkyl or branched $C_3$–$C_6$-alkyl, $C_6$–$C_{10}$-aryl, $C_4$–$C_{10}$-heteroaryl and/or $CO_2R^6$, and/or contains nonadjacent O, S and/or N atoms.

The term "bivalent hydrocarbon radical" also includes in this connection aryl, alkylaryl, (alkyl)cycloalkyl and optionally partially unsaturated (alkyl)heterocycloalkyl groups. The term "heteroaryl" includes partially or completely unsaturated cyclic systems which contain 4 to 10 C atoms and one or more nonadjacent O, N or S atoms or N(H) groups.

The compounds of the general formula (Ib) which are preferably employed are those in which $R^3$ is a linear bivalent $C_0$–$C_1$ or $C_5$–$C_{18}$ hydrocarbon radical which is optionally substituted by $CO_2R^6$ and/or contains nonadjacent O, S and/or N atoms.

Examples of suitable diamines of the general formula (Ib) are ethylenediamine, 1,4-diaminobutane, 1,8-diaminooctane and spermine.

3) Method for preparing primary alcohols $R^4$—$CH_2$—OH from amines $R^4$—$CH_2$—$NH_2$ comprising the following steps:
 a) oxidation of the aminomethyl group of an amine $R^4$—$CH_2$—$NH_2$ to a formyl group in the presence of a lysine oxidase as catalyst;
 b) Reduction of the formyl group resulting from a) with a reducing agent to a hydroxylmethyl group to form a primary alcohol $R^4$—$CH_2$—OH;

wherein the method is carried out as one-pot method, lysine oxidize and reducing agent are present together, and $R^4$ is a linear $C_1$–$C_{20}$ hydrocarbon radical which is optionally substituted by functional groups such as $CO_2H$ and/or $CO_2R^6$ (with $R^6$=linear $C_1$–$C_6$-alkyl or branched $C_3$–$C_6$-alkyl or $C_6$–$C_{10}$-aryl) and/or contain nonadjacent O, S and/or N atoms.

The term "linear hydrocarbon radical" also includes linear (alkyl)aryl groups, linear (alkyl)cycloalkyl groups and linear (alkyl)heterocycloalkyl groups.

Examples of suitable amines $R^4$—$CH_2$—$NH_2$ are n-butylamine, ethanolamine, glycine ethyl ester, 3-aminomethylpyridine and benzylamine.

The invention also relates to the use of a lysine oxidase in methods for reacting (di)arnines to give cyclic secondary amines, diols or alcohols in the presence of a reducing agent.

Lysine oxidases catalyze in vivo the oxidation of the ∊-amino group of lysine to aldehydes and thus initiate the stabilization of colagen and elastin fibers through formation of covalent crosslinks (Am. J. Respir. Cell Mol. Biol. 1991, 5, 206–210).

The lysine oxidases (E.C. class 1.4.3) generally employed for the methods of the invention are of microbial origin, i.e. from eukaryotes such as fungi or yeasts or prokaryotes such as Gram-positive or Gram-negative bacteria or archaebacteria. Lysine oxidases from yeasts of the general Candida, Hansenula, Pichia, Sporobolomyces, Sporopachydermia or Trigonopsis are preferably used. Particularly preferred lysine oxidases are those from the general and species *Candida nagoyaensis, Candida nemodendra, Candida boidinii, Candida lipolytica, Candida steatolytica, Candida tropicalis, Candida utilis, Hansenula minuta, Hansenula polymorpha, Pichia pinus, Pichia pastoris, Sporobolomyces alborubescens, Sporopachydermia cereana* or *Trigonopsis variabilis*. The lysine oxidase from the genus and species *Pichia pastoris* is very particularly preferred for the method of the invention.

It is possible to employ both unpurified crude enzymes and purified enzymes. All organisms or cells can also be used for the method of the invention as long as the enzymes are secreted into the extracellular medium or the cells have been permeabilized. The method of the invention is preferably carried out with purified enzymes.

It is advantageous that lysine oxidases can be obtained on the large scale by fermentation processes. For example, lysine oxidases from yeasts are obtained by fermenting the yeast which secretes the desired lysine oxidase in a nutrient medium containing yeast extract, soybean oil and conventional additives such as mineral salts and trade elements and, where appropriate, buffer substances. After the fermentation process, the lysine oxidases are released by a cell disruption which is carried out by conventional methods known to the skilled worker. After subsequent centrifugation, the supernatant solution is purified by ion exchange chromatography with subsequent molecular sieve chromatography and then a further ion exchange chromatography. It is possible thereby to prepare lysine oxidases with a purity of more than 90%, preferably of more than 95%, particularly preferably of more than 99%. In place of ion-exchange chromatography and molecular sieve chromatography it is also possible to purify by hydrophobic chromatography and precipitation methods.

For the reaction of the (di)amines in the methods of the invention, the lysine oxidase is generally employed in a concentration of from 2 to 20 units per mmol of substrate. 1 unit is defined as the amount of enzyme which catalyzes the formation of 1 µmol of $H_2O_2$ per minute at 30° C.

The reducing agents employed are generally those allowing the reaction to be carried out in aqueous medium. Examples thereof are the alkali metal and alkaline earth metal borohydrides, triacetoxyborohydrides, cyanoborohydrides and dithionites. In place of the alkali metal or alkaline earth metal salts, it is also possible to employ the transition metal salts of transition metals such as zinc, iron, manganese. The use of alkali metal salts is preferred, especially of $NaBH_4$. The reducing agent is generally employed in a concentration of ≦1% by weight, preferably in a concentration of ≦0.5% by weight based on the total amount of reaction medium. The total amount of reaction medium comprises the solution in which the reaction is carried out and, where appropriate, buffer substances, substrate, lysine oxidase and reducing agent present therein.

The reaction is generally carried out in aqueous solutions containing buffer substances. Suitable buffer substances are all buffer substances which buffer a pH range from 6.5 to 7.4, preferably a pH range from 6.8 to 7.2. Suitable buffer substances are the organic buffer substances known as Good's buffers, and phosphate/diphosphate buffers. Buffer substances containing amino groups, and potassium sodium phosphate/disphosphate are preferred, and trishydroxymethylaminomethane (called TRIS buffer) is particularly preferred. Other suitable buffer substances which buffer in the range between pH 6.5 and pH 7.4 can be found in standard works of reference.

In one embodiment of the invention, the reaction is carried out by adding the (di)amine to the stirred buffer solution containing lysine oxidase and reducing agent. In another embodiment of the invention, the lysine oxidase and the reducing agent are added simultaneously to the stirred (di)amine.

Said reducing agents are for the most part commercially available as solutions or suspensions in organic solvents such as glymes (glycol ethers), lower alcohols or dioxane, and are employed in this form. However, it is also possible to employ aqueous solutions of the reducing agents.

Addition of the reactants can take place both continuously and discontinuously, and preferably takes place discontinuously.

The lysine oxidase can be recovered for example by ultrafiltration and chromatography.

The method of the invention can generally be carried out at temperatures between 0 and 60° C., preferably between 10 and 40° C., particularly preferably between 20 and 30° C.

The method can be carried out both under atmospheric pressure and. under elevated pressure of up to 2 bar, but it is preferably carried out under atmospheric pressure.

The invention is now additionally illustrated in detail by the following examples.

EXEMPLARY EMBODIMENTS

Example 1

Preparation of the Lysine Oxidase from *Pichia pastoris*

1.a) Preparation of the Yeast Culture
 3 g/l Difco malt extract,
 5 g/l Difco peptone,
 3 g/l Difco yeast extract and
 20 g/l Difco agar were cultivated on YM agar plates. For this purpose, the plates were incubated at 28° C. for 48 hours and can then be kept at 4 to 5° C. for at least 4 weeks.

1.b) Preparation of the Preculture and of the Fermentation Medium
 b1) 10 g/l glucose are autoclaved at 121° C. for 30 minutes.
 b2) 0.2 g/l $MgSO_4.7H_2O$,
  3.0 g/l $KH_2PO_4$,
  0.2 ml/l of a Vishniac & Santer salt solution containing 50 g/l Titriplex III, 22 g/l $ZnSO_4.7H_2O$, 5.54 g/l $CaCl_2$, 5.06 g/l $MnCl_2.4H_2O$, 4.99 g/l $FeSO_4.7H_2O$, ammonium heptamolybdate.$4H_2O$, 1.57 g/l $CuSO_4.5H_2O$, 1.61 g/l $CoCl_2.6H_2O$ and adjusted with KOH to pH 6.0, were autoclaved at 121° C. for 30 minutes.
 b3) 10 ml/l of a Lodder vitamin solution containing 20 μg/l biotin, 20 mg/l calcium pantothenate, 2 μg/l folic acid, 10 mg/l inositol, 200 μg/l p-aminobenzoic acid, 400 μg/l nicotinic acid, 400 μg/l pyridoxine hydrochloride, 200 μg/l riboflavin and 400 μg/l thiamine hydrochloride were sterilized by filtration.

Medium ingredients b1) to b3) were combined after the sterilization.

500 ml of this fermentation medium were transferred into a 1 l Erlenmeyer flask. From 3 to 4 agar plates containing the Pichia pastoris yeast culture (see 11.a)) the yeast cells were removed with an inoculation needle and transferred into said Erlenmeyer flask. The incubation was carried out at 28° C. and 200 revolutions per minute for 24 hours.

1.c) Preparation of the Main Culture

The preculture prepared in 1.b) was transferred into a 10 l fermenter and diluted with water. The pH was adjusted to about 7.0 by adding 50% by volume aqueous n-butylamine solution. The fermentation was carried out at a temperature of 28° C. and with aeration at 5 l/min at 400 revolutions per minute for about 28 to 30 hours. The time to stop the fermentation was found by determining the absorption at 600 nm (OD 600; OD=optical density). The OD 600 of the fermenter samples was measured with air as reference and was intended to be 0.9 to 1.0.

For workup, the contents of the fermenter were centrifuged at 45° C. and 5 000 revolutions per minute (about 95 000 g; g=acceleration due to the gravity) for 20 minutes. The supernatant solution was removed, and the residue was washed with 250 ml of 50 millimolar potassium phosphate/potassium diphosphate buffer solution and centrifuged again. The supernatant solution was again removed, and the biomass remaining in the residue was stored in a deepfreeze at −15° C.

1.d) Cell Disruption and Homogenization 18 ml of the *Pichia pastoris* biomass which had been stored at −20° C. and thawed were diluted with a buffer solution containing 20 mmol/l sodium phosphate and 1 mmol/l ethanolamine (pH 7.0) to 50 ml. 50 of glass beads with a diameter of 0.5 mm were added to this solution, and the mixture was homogenized at 5 000 revolutions per minute and 0° C. for 30 minutes. The homogenate was filtered through gauze. The filtrate was centrifuged at 8 000 revolutions per minute and 4° C. for 10 minutes. The supernatant was removed.

Example 2

Purification of the Lysine Oxidase from *Pichia pastoris*

2.a) Ion Exchange Chromatography

The removed supernatant was adjusted to pH 7.0 with NaOH and loaded onto a Q-Sepharose fast flow column from Pharmacia with a diameter of 5 cm, a height of 13 cm and a volume of 250 ml. After loading, the column was washed with 600 ml of solution A. Solution A contains sodium phosphate in a concentration of 20 mmol/l and ethanolamine in a concentration of 1 mmol/l. Solution B contains sodium phosphate in a concentration of 20 mmol/l, ethanolamine in a concentration of 1 mmol/l and NaCl in a concentration of 1 mol/l. A linear gradient of 1 l of solution A and 1 l of solution B was used for elution. The active fractions were collected.

2.b) Molecular Sieve Chromatography

The active fractions were filtered through a 10 Da Omega filter (ultrafiltration) and separated on a preparative Superdex column from Pharmacia with a diameter of 2.6 cm, a length of 60 cm and a volume of 320 ml. The mobile phase used was a solution containing 20 mmol/l sodium phosphate/sodium diphosphate buffer, 150 mmol/l NaCl and 1 mmol/l ethanolamine with a pH of 7.5. The mobile phase was passed through the column at a rate of 3 ml/min. The active fractions were determined by the method described under 2.d) and combined.

2.c) Ion Exchange Chromatogaphy

The combined active fractions obtained under 2.b) were further purified by chromatography on a Mono-Q HR5/5 column from Pharmacia. A mixture of solution A and solution B was used as mobile phase. This was passed through a column at a rate of 1 mil/min, and 100 fractions each of 1 ml were collected. The active fractions were likewise determined by the method described under 2.d) and combined. The lysine oxidase eluted as active main protein. The protein had a molecular weight of about 121 000 Da in an SDS gel under reducing conditions, for example through addition of β-mercaptoethanol or dithiothreitol.

2.d) Determination of the Lysine Oxidase Activity

The active fractions, that is to say the lysine oxidase activity were determined by utilizing the conversion of benzylamine into benzaldehyde in the presence of lysine oxidase. Benzaldehyde is UV-active and can be detected at 250 nm. An aliquot of the fractions collected under 2.a) to 2.c) was incubated in each case with 3 mmol of benzylamine in a phosphate/dihydrogen phosphate buffer for 1 to 5 hours. The solution obtained in this way was analyzed in an HPLC system using a Li-Chrosorb 5RP C18 chromatography column from Merck. Water containing 0.1% by volume of trifluoroacetic acid was used as mobile phase A, and acetonitrile containing 0.1% by volume of trifluoroacetic acid was used as mobile phase B.

TABLE 1

HPLC program

| Time [min] | Mobile phase [% B] | Flow rate [ml/min] |
|---|---|---|
| 0 | 40 | 1 |
| 6 | 70 | 1 |
| 6.1 | 100 | 1 |
| 6.5 | 100 | 1.5 |
| 9 | 40 | 1.5 |

The amount of benzaldehyde produced was determined from a calibration plot (1-100 µmol).

2.e) Determination of the Amino Acid Sequence

In the Edman degradation of the lysine oxidase from *Pichia pastoris*, an amino-terminal sequence with the sequence SEQ ID NO 1 (see sequence listing) was obtained. Partial sequences SEQ ID NO 2 to 12 (see sequence listing) were obtained by proteolytic degradation of the lysine oxidase from Pichia pastoris with trypsin.

Example 3

Determination of the Enzymatic Activity in the Presence and Absence of Reducing Agent 3.a) Assays with Various Substrates The substrates employed were L-lysine monohydrochloride (for biochemical purposes, 99% from Merck), ethanolamine from BASF AG, glycine ethyl ester, 1,8-diaminooctane from Aldrich, n-butylamine from BASF AG, 1,4-diaminobutane from BASF AG, ethylenediamine from BASF AG, spermine from Aldrich, 3-aminomethylpyridine from Aldrich, benzylamine from Aldrich, L-(+)-ornithine hydrochloride (99% from Aldrich) and 1,6-diaminohexane from BASF AG.

Measurement series in each case with a concentration of 1 200, 600, 300, 150, 75, 37.5 and 18.75 µmol of (di)amine per 1 l of water were carried out in a microtiter plate. 2 measurement series were carried out in each case; one with enzyme and one without enzyme as reference.

100 µl of each of the diluted solutions were taken. To this solution were added 25 µl of lysine oxidase and 40 µl of 35 millimolar phenol solution in 200 millimolar potassium phosphate/potassium diphosphate solution with a pH of 7.5, 40 µl of a 2 millimolar aqueous 4-aminoantipyrine solution and 40 µl of a solution of 0.35 mg of peroxidase (horseradish from Sigma) in 1 ml of water.

In the reference measurement series, the 25 µl of lysine oxidase were replaced by 25 µl of water. A violet dye was formed by the ammonia produced on conversion of the substrates and its absorption in the UV at 500 nm was measured (T. Uwajima, O. Terada, Methods in Enzymology 1982, 89, 243 ff.).

The relative conversion rates of the substrates compared with L-lysine are to be found in table 1.

TABLE 1

| Substrate to be converted | Relative conversion rate compared with L-lysine in % |
|---|---|
| L-Lysine | 100 |
| α-N-Acetyllysine | 120 |
| D-Lysine | 100 |
| D/L-5-Hydroxylysine | 60 |
| L-Ornithine | 90 |
| D-Ornithine | 90 |

TABLE 1-continued

| Substrate to be converted | Relative conversion rate compared with L-lysine in % |
|---|---|
| D/L-Ornithine difluoromethyl ester | 39 |
| 1,6-Diaminohexane | 180 |
| Ethylenediamine | 84 |
| 1,4-Diaminobutane | 133 |
| 1,8-Diaminooctane | 197 |
| Spermine | 185 |
| n-Butylamine | 63 |
| Ethanolamine | 50 |
| Glycine ethyl ester | 93 |
| 3-Aminomethylpyridine | 128 |
| Benzylamine | 108 |

It emerged that both (un)substituted aliphatic amines and diamines, and amino acids and their derivatives can be converted in the presence of lysine oxidase. Remarkably, the conversion rate of some substrates is increased by comparison with L-lysine. The use of derivatives of lysine and ornithine is of particular interest in relation to the preparation of piperidine-2-carboxylic acid and proline derivatives.

3.b) Assay with Various Concentrations of Reducing Agent

In order to test the tolerance of lysine oxidases to reducing agents, by way of example the measurement series with L-lysine using the lysine oxidase from Pichia pastoris was repeated in the presence of 0.001% by weight, 0.01% by weight, 0.1% by weight, 0.5% by weight and 1% by weight of $NaBH_4$ based on the total amount of substrate solution. The results are to be found in table 2.

TABLE 2

| Lysine oxidase from Pichia pastoris | Activity in U/l | pH during incubation | Conversion in % |
|---|---|---|---|
| Without $NaBH_4$ | 277 | ~7 | 100.0 |
| +0.001 wt. % $NaBH_4$ | 271 | ~7 | 97.8 |
| +0.01 wt. % $NaBH_4$ | 276 | ~7 | 99.6 |
| +0.1 wt. % $NaBH_4$ | 276 | ~7 | 99.6 |
| +0.5 wt. % $NaBH_4$ | 203 | ~8.5 | 73.3 |
| +1 wt. % $NaBH_4$ | 167 | ~9–10 | 60.3 |

It emerged that the activity of the lysine oxidase remained virtually unchanged up to a concentration of 0.1% by weight $NaBH_4$. At concentrations of $\geq 0.5\%$ by weight $NaBH_4$, the activity decreased because of the increase in the pH. Relatively good conversions were still achieved up to an $NaBH_4$ concentration of 1% by weight. Thus 1% by weight $NaBH_4$, based on the total amount of the substrate solution, was employed in each of the subsequent tests.

3.c) Workup of the Samples 50 ml of a 1.2 millimolar L-lysine solution converted in the presence of lysine oxidase was evaporated to dryness, taken up in five times the amount of ethanol, mixed with 1 drop of concentrated sulfuric acid and left to stand at room temperature overnight. After removal of the ethanol by distillation in vacuo, the residue was mixed with an excess of triethylamine and benzyl chloroformate and left to react at room temperature for 3 h. After addition of water, the N-benzyloxycarbonyl derivatives wee extracted with dichloromethane. The organic phase was characterized by mass spectrometry and NMR. The resulting spectra corresponded to those of authentic samples of piperidine-2-carboxylic acid.

The other substrate solutions were worked up analogously.

We claim:

1. A method for reacting amines of the general formula (I)

$$A-CH_2-NH_2 \quad (I)$$

with A- meaning

to give compounds of the general formula (II) or (III)

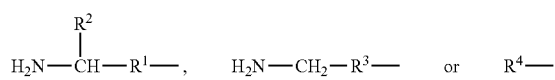

$$B-CH_2-OH \quad (III)$$

with B- meaning HO—CH$_2$—R$^3$— or R$^4$— comprising the following steps:

a) oxidation of at least one

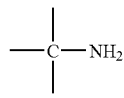

group of an amine of the general formula (I) to a carbonyl group in the presence of a lysine oxidase as catalyst;

b) where appropriate reaction of the second NH$_2$ group of an amine of the general formula (I) with

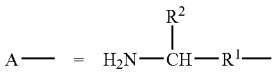

with the carbonyl group resulting from a) to give an enamine or imine by cyclization;

c) reduction of the carbonyl group(s) resulting from a), or of the anamine or imine resulting where appropriate from b), with a reducing agent respectively to hydroxymethyl groups or to a cyclic secondary amine of the general formula (II), where R$^1$ is NR$^5$ or a linear bivalent C$_2$–C$_6$ hydrocarbon radical which is optionally substituted by CO$_2$H, C$_2$R$^6$, OH, SH and/or N(R$^5$)$_2$ and/or contains nonadjacent O, S and/or N atoms, where R$^5$ is H or linear C$_1$–C$_6$-alkyl and R$^6$ is linear C$_1$–C$_6$-alkyl or branched C$_3$–C$_6$-alkyl or C$_6$–C$_{10}$-aryl, and R$^2$ is H, CO$_2$H, C$_2$R$^6$ or CN, where the method is carried out as a one-pot method, lysine oxidise and reducing agent are present together, and in the definition of A in the general formula (I)

R$^3$ is a bivalent C$_0$–C$_1$ or C$_5$–C$_{18}$ hydrocarbon radical which is optionally substituted by linear C$_1$–C$_6$-alkyl or branched $C_3$–$C_6$-alkyl, $C_6$–$C_{10}$-aryl, $C_4$–$C_{10}$-heteroaryl and/or $CO_2R^6$ and/or contains nonadjacent O, S and/or N atoms, and $R^4$ is a linear $C_1$–$C_{20}$ hydrocarbon radical which is optionally substituted by functional groups $CO_2H$ and/or $CO_2R^6$ and/or contains nonadjacent O, S and/or N atoms.

2. A method for preparing cyclic secondary amines of the general formula (II) from diamines of the general formula (Ia)

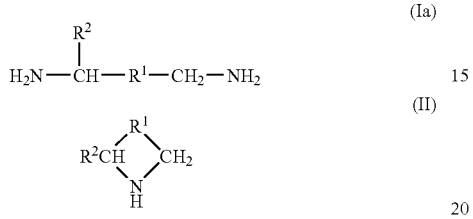

(Ia)

(II)

where $R^1$ is $NR^5$ or a linear bivalent hydrocarbon radical with 2 to 6 C atoms, which is optionally substituted by functional groups $CO_2H$, $C_2R^6$, OH, SH and/or $N(R^5)_2$, and/or contains nonadjacent heteroatoms O, S and/or N, p1 where $R^5$ is H or linear $C_1$–$C_6$-alkyl and $R^6$ is linear $C_1$–$C_6$-alkyl or branched $C_3$–$C_6$-alkyl or $C_6$–$C_{10}$-aryl, and $R^2$ is H, $CO_2H$, $C_2R^6$ or CN, comprising the following steps:

oxidation of one of the two

groups of a dimaine of the general formula (Ia) to a carbonyl group in the presence of a lysine oxidase as catalyst;

b) reaction of the second $NH_2$ group of the diamine of the general formula (Ia) with the carbonyl group resulting from step a) to give an enamine or imine by cyclization;

c) reduction of the enamine or imine resulting from b) with a reducing agent to give a cyclic secondary amine of the general formula (II);

wherein the method is carried out as one-pot method, and lysine oxidase and reducing agent are present together.

3. A method as claimed in claim 2, wherein the diamine of the general formula (Ia) is selected from the group consisting of lysine, omithine and 1,6-diaminohexane.

4. A method for preparing diols of the general formula (IIIa) from diamines of the general formula (Tb)

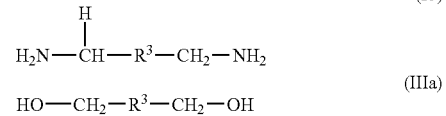

(Ib)

(IIIa)

comprising the following steps:
a) oxidation of the two aminomethyl groups of a diamine of the general formula Ib) to formyl groups in the presence of a lysine oxidizase as catalyst;
b) reduction of the formyl groups resulting from a) with a reducing agent to hydroxymethyl groups to form a diol of the general formula (IIIa);
wherein the method is carried out as one-pot method, lysine oxidize and reducing agent are present together, and $R^3$ is a bivalent $C_0$–$C_1$ or $C_5$–$C_{18}$ hydrocarbon radical which is optionally substituted by linear $C_1$–$C_6$-alkyl or branched $C_3$–$C_6$-alkyl, $C_6$–$C_{10}$-aryl, $C_4$–$C_{10}$-heteroaryl and/or $CO_2R^6$, and/or contains nonadjacent O, S and/or N atoms, wherein $R^6$ is linear $C_1$–$C_6$-alkyl or branched $C_3$–$C_6$-alkyl or $C_6$–$C_{10}$-aryl.

5. A method for preparing primary alcohols $R^4$—$CH_2$—OH from amines $R^4$—$CH_2$—$NH_2$ comprising the following steps:
a) oxidation of the aminomethyl group of an amine $R^4$—$CH_2$—NH2 to a formyl group in the presence of a lysine oxidase as catalyst;
b) reduction of the formyl group resulting from a) with a reducing agent to a hydroxylmethyl group to form a primary alcohol $R^4$—$CH_2$—OH;
wherein the method is carried out as one-pot method, lysine oxidase and reducing agent are present together, and $R^4$ is a linear $C_1$–$C_{20}$ hydrocarbon radical which is optionally substituted by functional groups $CO_2H$ and/or $CO_2R^6$ and/or contains nonadjacent O, S and/or N atoms, wherein $R^6$ is linear $C_1$–$C_6$-alkyl or branched $C_3$–$C_6$-alkyl or $C_6$–$C_{10}$-aryl.

6. A method as claimed in claim 1, wherein a lysine oxidase from a yeast is employed.

7. A method as claimed in claim 2, wherein a lysine oxidase from a yeast is employed.

8. A method as claimed in claim 3, wherein a lysine oxidase from a yeast is employed.

9. A method as claimed in claim 4, wherein a lysine oxidase from a yeast is employed.

10. A method as claimed in claim 5, wherein a lysine oxidase from a yeast is employed.

11. The method of any of claims 6, 7, 8, 9, or 10, wherein said yeast is Pichia pastoris.

* * * * *

UNITED STATES PATENT AND TRADEMARK OFFICE
CERTIFICATE OF CORRECTION

| | | |
|---|---|---|
| PATENT NO. | : 7,229,803 B2 | Page 1 of 1 |
| APPLICATION NO. | : 10/474601 | |
| DATED | : June 12, 2007 | |
| INVENTOR(S) | : Thomas Friedrich et al. | |

It is certified that error appears in the above-identified patent and that said Letters Patent is hereby corrected as shown below:

In the Claims:

At column 16, line 55, replace "$C_2R^6$" with --$CO_2R^6$--

At column 16, line 61, replace "$C_2R^6$" with --$CO_2R^6$--

At column 17, line 24, replace "$C_2R^6$" with --$CO_2R^6$,--

At column 17, line 26, remove "p1" so it should correctly appear as --O,S and/or N, where--;

At column 17, line 29, replace "$C_2R^6$" with --$CO_2R^6$--

At column 17, line 53, replace "omithine" with --ornithine--

Signed and Sealed this

Twentieth Day of November, 2007

JON W. DUDAS
*Director of the United States Patent and Trademark Office*